US011071460B2

(12) United States Patent
Irisawa et al.

(10) Patent No.: US 11,071,460 B2
(45) Date of Patent: Jul. 27, 2021

(54) PHOTOACOUSTIC MEASUREMENT APPARATUS AND PHOTOACOUSTIC MEASUREMENT SYSTEM

(71) Applicant: FUJIFILM Corporation, Tokyo (JP)

(72) Inventors: Kaku Irisawa, Ashigarakami-gun (JP); Dai Murakoshi, Ashigarakami-gun (JP); Tetsuro Ebata, Ashigarakami-gun (JP); Shoji Hara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1038 days.

(21) Appl. No.: 15/639,026

(22) Filed: Jun. 30, 2017

(65) Prior Publication Data

US 2017/0296062 A1    Oct. 19, 2017

Related U.S. Application Data

(63) Continuation of application No. PCT/JP2015/084146, filed on Dec. 4, 2015.

(30) Foreign Application Priority Data

Jan. 8, 2015 (JP) .............................. JP2015-002196

(51) Int. Cl.
*A61B 8/00* (2006.01)
*A61B 5/02* (2006.01)
(Continued)

(52) U.S. Cl.
CPC ............ *A61B 5/0095* (2013.01); *A61B 5/026* (2013.01); *A61B 5/0261* (2013.01); *A61B 8/06* (2013.01);
(Continued)

(58) Field of Classification Search
CPC ..... A61B 5/0095; A61B 5/026; A61B 5/0261; A61B 5/06
See application file for complete search history.

(56) References Cited

U.S. PATENT DOCUMENTS

2006/0052714 A1*  3/2006  Poliac ................ A61B 5/02225
                                                            600/492
2008/0269605 A1* 10/2008  Nakaya ................ A61B 5/6844
                                                            600/437
(Continued)

FOREIGN PATENT DOCUMENTS

JP    2009-506871 A    2/2009
JP    2012-113191 A    6/2012

OTHER PUBLICATIONS

"Favazza et al.," In vivo functional photoacoustic microscopy of cutaneous microvasculature in human skin, Journal of Biomedical Optics 16(2), 026004 Feb. 2011.*
(Continued)

*Primary Examiner* — Patricia J Park
(74) *Attorney, Agent, or Firm* — Birch, Stewart, Kolasch & Birch, LLP

(57) ABSTRACT

In a photoacoustic measurement apparatus and a photoacoustic measurement system, it is possible to generate blood flow information using a photoacoustic image without requiring a separate tourniquet. A light source emits measurement light. A probe detects a photoacoustic wave generated in a subject after measurement light is emitted to the subject in each of the avascularized condition in which the subject is avascularized and the non-avascularized condition in which the subject is not avascularized. Photoacoustic image generation unit generates a photoacoustic image based on the detection signal of the photoacoustic wave. Blood flow information generation unit generates blood flow information based on the signal value of a photoacoustic
(Continued)

image in a region of interest set in the photoacoustic image. The avascularization of the subject is performed by pressing the probe against the subject.

23 Claims, 5 Drawing Sheets

(51) Int. Cl.
    *A61B 8/06*     (2006.01)
    *A61B 5/00*     (2006.01)
    *A61B 5/026*     (2006.01)
    *A61B 8/08*     (2006.01)

(52) U.S. Cl.
    CPC .......... *A61B 8/0891* (2013.01); *A61B 5/6843* (2013.01); *A61B 2562/14* (2013.01)

(56) References Cited

U.S. PATENT DOCUMENTS

| | | | | |
|---|---|---|---|---|
| 2008/0298642 A1* | 12/2008 | Meenen | ................... | G06K 9/00 382/115 |
| 2009/0246797 A1* | 10/2009 | Campbell | .......... | A61B 5/14546 435/7.1 |
| 2013/0030268 A1* | 1/2013 | Saito | ........................ | A61B 1/05 600/325 |
| 2014/0142404 A1* | 5/2014 | Wang | .................. | A61B 8/4416 600/324 |
| 2014/0371589 A1* | 12/2014 | Nakabayashi | ......... | A61B 8/406 600/442 |
| 2015/0190111 A1* | 7/2015 | Fry | ........................ | A61B 5/022 600/438 |

OTHER PUBLICATIONS

International Search Report (PCT/ISA/210) issued in PCT/JP2015/084146, dated Feb. 9, 2016.
Written Opinion of the International Searching Authority (PCT/ISA/237) issued in PCT/JP2015/084146, dated Feb. 9, 2016.
International Preliminary Report on Patentability and English translation of the Written Opinion of the International Searching Authority (Forms PCT/IB/373 and PCT/ISA/237), dated Jul. 11, 2017, for International Application No. PCT/JP2015/084146.

\* cited by examiner

FIG. 3
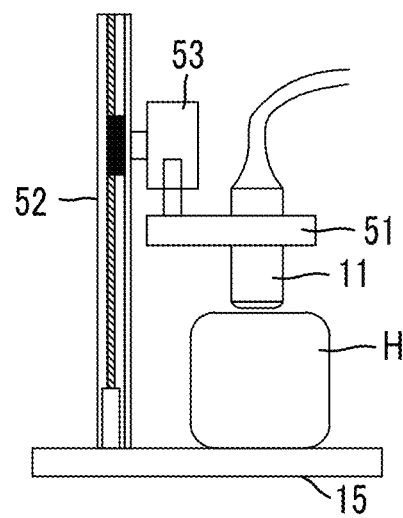
FIG. 4
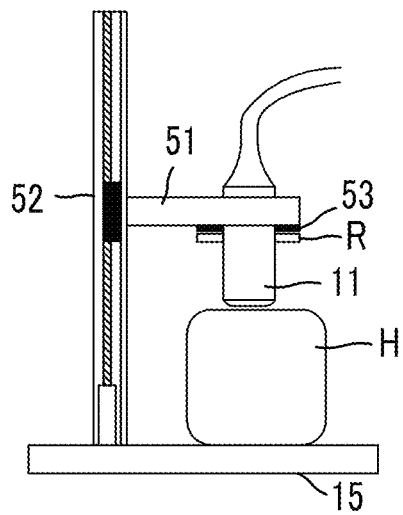
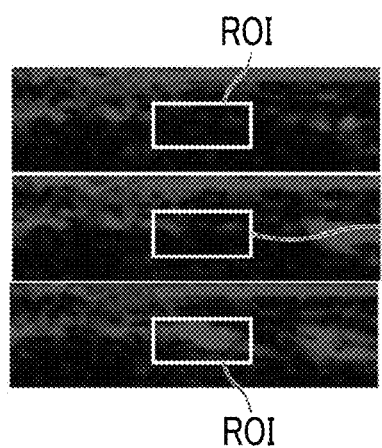
FIG. 5A
FIG. 5B
FIG. 5C

PHOTOACOUSTIC MEASUREMENT APPARATUS AND PHOTOACOUSTIC MEASUREMENT SYSTEM

CROSS-REFERENCE TO RELATED APPLICATIONS

This application is a Continuation of PCT International Application No. PCT/JP2015/084146 filed on Dec. 4, 2015, which claims priority under 35 U.S.C § 119(a) to Japanese Patent Application No. 2015-002196 filed on Jan. 8, 2015. Each of the above application(s) is hereby expressly incorporated by reference, in its entirety, into the present application.

BACKGROUND OF THE INVENTION

1. Field of the Invention

The present invention relates to a photoacoustic measurement apparatus and a photoacoustic measurement system, and more particularly, to a photoacoustic measurement apparatus and a photoacoustic measurement system for detecting photoacoustic waves generated in a subject after emitting light to the subject.

2. Description of the Related Art

As a prior art that restricts a blood flow from the outside and releases the restriction to evaluate the perfusion state of the blood flow, a skin perfusion pressure (SPP) measuring apparatus is known (for example, JP2009-506871A). The SPP measuring apparatus emits laser light to a measurement part. The amount and the Doppler shift of reflected light with respect to the emitted laser light change according to a blood flow. The amount and the Doppler shift of reflected light are measured while changing the cuff pressure from high pressure to low pressure, a cuff pressure at which the blood flow abruptly increases is calculated, and the cuff pressure is displayed as "skin perfusion pressure".

For the observation of the blood flow, JP2012-113191A discloses a method of generating a blood flow image. In JP2012-113191A, a blood flow image is generated by capturing a reflection type confocal laser microscope image of the skin as a motion picture, generating a plurality of brightness difference images between frames of the motion picture, and adding the plurality of brightness difference images. JP2012-113191A discloses temporarily stopping the skin blood flow of the forearm (measurement part), which is distal when viewed from the heart, by wrapping a cuff around the subject's upper arm and pressing it and then releasing the pressure to return to the skin blood flow (reperfusion). JP2012-113191A discloses generating a blood flow image before the press, during the press, and immediately after reperfusion.

Here, as a kind of image examination method capable of examining the state of the inside of a living body in a non-invasive manner, photoacoustic imaging for imaging the inside of the living body by using the photoacoustic effect is known. In general, in photoacoustic imaging, pulsed laser light, such as a laser pulse, is emitted into the living body. In the living body, once a living tissue absorbs the energy of the pulsed laser light, and then ultrasound waves (photoacoustic waves) are generated due to adiabatic expansion immediately occurs. By detecting the photoacoustic waves using an ultrasound probe or the like and generating a photoacoustic image based on the detection signal, it is possible to visualize the inside of the living body based on the photoacoustic waves.

SUMMARY OF THE INVENTION

In JP2009-506871A, since the blood flow is measured at one measurement point, it is not possible to evaluate the spatial distribution of perfusion. In particular, it is not possible to perform evaluation in a depth direction. In JP2012-113191A, it is possible to evaluate the spatial distribution of perfusion with a blood flow image. In JP2012-113191A, however, a reflection type confocal laser microscope is required. In JP2009-506871A and JP2012-113191A, in order to temporarily stop the blood flow, a tourniquet with variable cuff pressure is used. In JP2009-506871A and JP2012-113191A, it is necessary to separately prepare a tourniquet. Accordingly, for easy measurement, it is desirable to evaluate perfusion without requiring a tourniquet.

In view of the above circumstances, it is an object of the present invention to provide a photoacoustic measurement apparatus and a photoacoustic measurement system for generating blood flow information using a photoacoustic image without requiring a separate tourniquet.

In order to achieve the aforementioned object, the present invention provides a photoacoustic measurement apparatus comprising: a probe that detects a photoacoustic wave generated in a subject by measurement light emitted to the subject; a pressure detection unit for detecting a contact pressure of the probe with respect to the subject; a photoacoustic image generation unit for generating a photoacoustic image based on a detection signal of the photoacoustic wave detected by the probe; and a blood flow information generation unit for generating blood flow information based on a signal value of the photoacoustic image in a region of interest set in the photoacoustic image. The probe detects the photoacoustic wave in each of at least an avascularized condition in which the subject is avascularized by the probe and a non-avascularized condition in which the subject is not avascularized.

The photoacoustic measurement apparatus of the present invention may further comprise: a grip portion that grips the probe; and a moving mechanism that moves the probe in a direction in which the probe is pressed against the subject and a direction in which the probe is away from the subject through the grip portion.

The photoacoustic measurement apparatus of the present invention may further comprise a contact pressure control unit for driving the moving mechanism based on the contact pressure detected by the pressure detection unit.

The pressure detection unit may detect the contact pressure of the probe at the grip portion.

Instead of the above, the pressure detection unit may be provided at the probe.

The probe may include a detector element that detects the photoacoustic wave and a light emitting portion that emits the measurement light, and at least a part of the pressure detection unit may be provided between the detector element and the light emitting portion.

The pressure detection unit may surround the detector element.

The pressure detection unit may be covered with a cover in contact with the subject.

The blood flow information generation unit may binarize the signal value by setting the signal value to a first value when the signal value is equal to or greater than a first threshold value and equal to or less than a second threshold value larger than the first threshold value and setting the signal value to a second value when the signal intensity is less than the first threshold value or greater than the second threshold value, and generate the blood flow information based on the binarized signal value.

The probe may further detect a reflected acoustic wave with respect to an acoustic wave transmitted to the subject. In this case, it is preferable that the photoacoustic measurement apparatus of the present invention further has a reflected acoustic wave image generation unit for generating a reflected acoustic wave image based on a detection signal of the reflected acoustic wave detected by the probe and a region-of-interest tracking unit for tracking a position of the region of interest using the reflected acoustic wave image.

The blood flow information generation unit may generate, as blood flow information, a total value or an average value of the signal value in the region of interest.

The blood flow information generation unit may further generate a graph showing a relationship between the blood flow information and the contact pressure.

The blood flow information generation unit may calculate a total value or an average value of the signal value in the region of interest, and generate, as the blood flow information, a score value based on a difference between a minimum value and a maximum value of the total value or the average value in a certain period.

The blood flow information generation unit may generate, as the blood flow information, a score value based on a difference between a total value or an average value of the signal value in the region of interest in the avascularized condition and a total value or an average value of the signal value in the region of interest in the non-avascularized condition.

In a case where the subject is changed from the avascularized condition to the non-avascularized condition by the probe, the blood flow information generation unit may generate, as the blood flow information, a score value based on a time change rate of a total value or an average value of the signal value in the region of interest.

In a case where the subject is changed from the avascularized condition to the non-avascularized condition by the probe, the blood flow information generation unit may generate, as the blood flow information, a score value based on a total value or an average value of the signal value in the region of interest after a certain time has passed from a reference time.

In a case where the subject is changed from the avascularized condition to the non-avascularized condition by the probe, the blood flow information generation unit may generate, as the blood flow information, a score value based on a time from a reference time to a time at which a total value or an average value of the signal value in the region of interest reaches a certain level.

The blood flow information generation unit may further generate a blood flow information image based on the blood flow information.

In a case where a plurality of the regions of interest are set, the blood flow information may be generated for each of the plurality of regions of interest, and the blood flow information image may be a space map image for displaying blood flow information of each region of interest in the region of interest.

In the blood flow information image, it is preferable that each region of interest is displayed with a brightness corresponding to the blood flow information.

The blood flow information generation unit may set a display color of each region of interest in the blood flow information image to a different display color in a case where blood flow information at a first time is larger than blood flow information at a second time earlier than the first time and a case where the blood flow information at the first time is smaller than the blood flow information at the second time.

It is preferable that a plurality of the regions of interest are set in a grid form.

In addition, the present invention provides a photoacoustic measurement system comprising: a light source that emits measurement light; a probe that detects a photoacoustic wave generated in a subject after the measurement light is emitted to the subject; a pressure detection unit for detecting a contact pressure of the probe with respect to the subject; a photoacoustic image generation unit for generating a photoacoustic image based on a detection signal of the photoacoustic wave detected by the probe; and a blood flow information generation unit for generating blood flow information based on a signal value of the photoacoustic image in a region of interest set in the photoacoustic image. The probe detects the photoacoustic wave in each of at least an avascularized condition in which the subject is avascularized by the probe and a non-avascularized condition in which the subject is not avascularized.

The photoacoustic measurement apparatus and the photoacoustic measurement system of the present invention can generate blood flow information using a photoacoustic image without requiring a separate tourniquet.

BRIEF DESCRIPTION OF THE DRAWINGS

FIG. 3 is a diagram showing how a photoacoustic wave is detected.

FIG. 4 is a diagram showing another example of the photoacoustic wave detection.

FIGS. 5A to 5C are diagrams showing a photoacoustic image and a region of interest.

DESCRIPTION OF THE PREFERRED EMBODIMENTS

Figure 1:
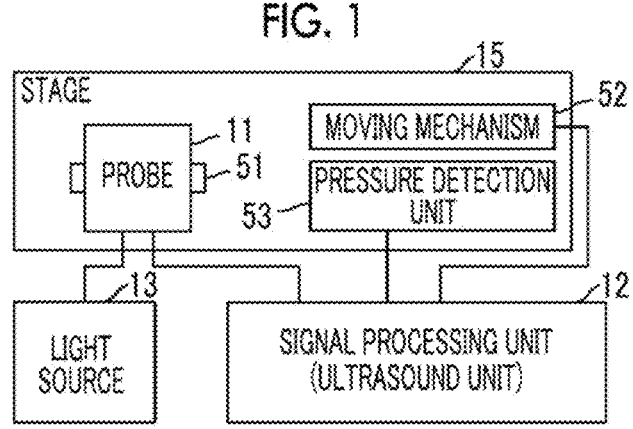
FIG. 1 is a block diagram schematically showing a photoacoustic measurement system including a photoacoustic measurement apparatus according to a first embodiment of the present invention.

Hereinafter, embodiments of the present invention will be described in detail with reference to the diagrams. FIG. 1 shows the schematic configuration of a photoacoustic measurement system including a photoacoustic measurement apparatus according to a first embodiment of the present invention. A photoacoustic measurement system 10 has a probe (ultrasound probe) 11, an ultrasound unit (signal processing unit) 12, a light source 13, and a stage 15.

The light source 13 emits measurement light. The measurement light emitted from the light source 13 is guided to the probe 11 using, for example, light guide means, such as an optical fiber, and is emitted from the probe 11 toward a subject. The light source 13 is, for example, a solid state laser light source using an yttrium aluminum garnet (YAG), alexandrite, or the like. The wavelength of measurement light is preferably a wavelength at which absorption in blood is stronger than that in the surrounding tissue, such as muscle or fat. Hereinafter, an example in which light having a wavelength of 755 nm is mainly used will be described. The type of the light source is not particularly limited, and the light source 13 may be a laser diode light source (semiconductor laser light source), or may be a light amplification type laser light source using a laser diode light source as a seed light source. Light sources other than the laser light source may be used.

The probe 11 is an acoustic wave detection unit, and has a plurality of detector elements (ultrasound transducers) arranged in a one-dimensional manner, for example. The probe 11 is not limited to the linear probe, but may be a convex probe or a sector probe. The probe 11 is disposed in a part (measurement part) for measuring the blood perfusion of the subject with echogel, water, or the like interposed therebetween. It is preferable that the probe 11 is disposed on the palm side where the amount of body hair or skin melanin is small.

The probe 11 detects photoacoustic waves generated in the subject after measurement light is emitted to the subject in each of the avascularized condition in which the subject is avascularized and the non-avascularized condition in which the subject is not avascularized. Here, the avascularized condition refers to a state in which the blood flow in the measurement part of the subject is at least partially stopped. Preferably, the avascularized condition refers to a state in which the subject is pressed with a pressure equal to or higher than the systolic blood pressure. The non-avascularized condition refers to a state in which the blood flow in the measurement part of the subject is not disturbed. Preferably, the non-avascularized condition refers to a state in which the subject is not pressed or the subject is pressed with a pressure equal to or lower than the diastolic blood pressure.

The stage 15 is a stage on which the subject is placed. The stage 15 includes a grip portion 51 for gripping the probe 11, a moving mechanism 52 for moving the probe 11 in a direction in which the probe 11 is pressed against the subject and a direction in which the probe 11 is away from the subject through the grip portion 51, a pressure detection unit 53 for detecting the contact pressure of the probe 11 with respect to the subject. In the present embodiment, the probe 11 is pressed against the subject with a pressure equal to or higher than the systolic blood pressure of the subject, thereby performing avascularization.

The ultrasound unit 12 processes the detection signal of photoacoustic waves detected by the probe. The ultrasound unit 12 forms a photoacoustic measurement apparatus. The ultrasound unit 12 typically has a processor, a memory, a bus, and the like.

Figure 2:
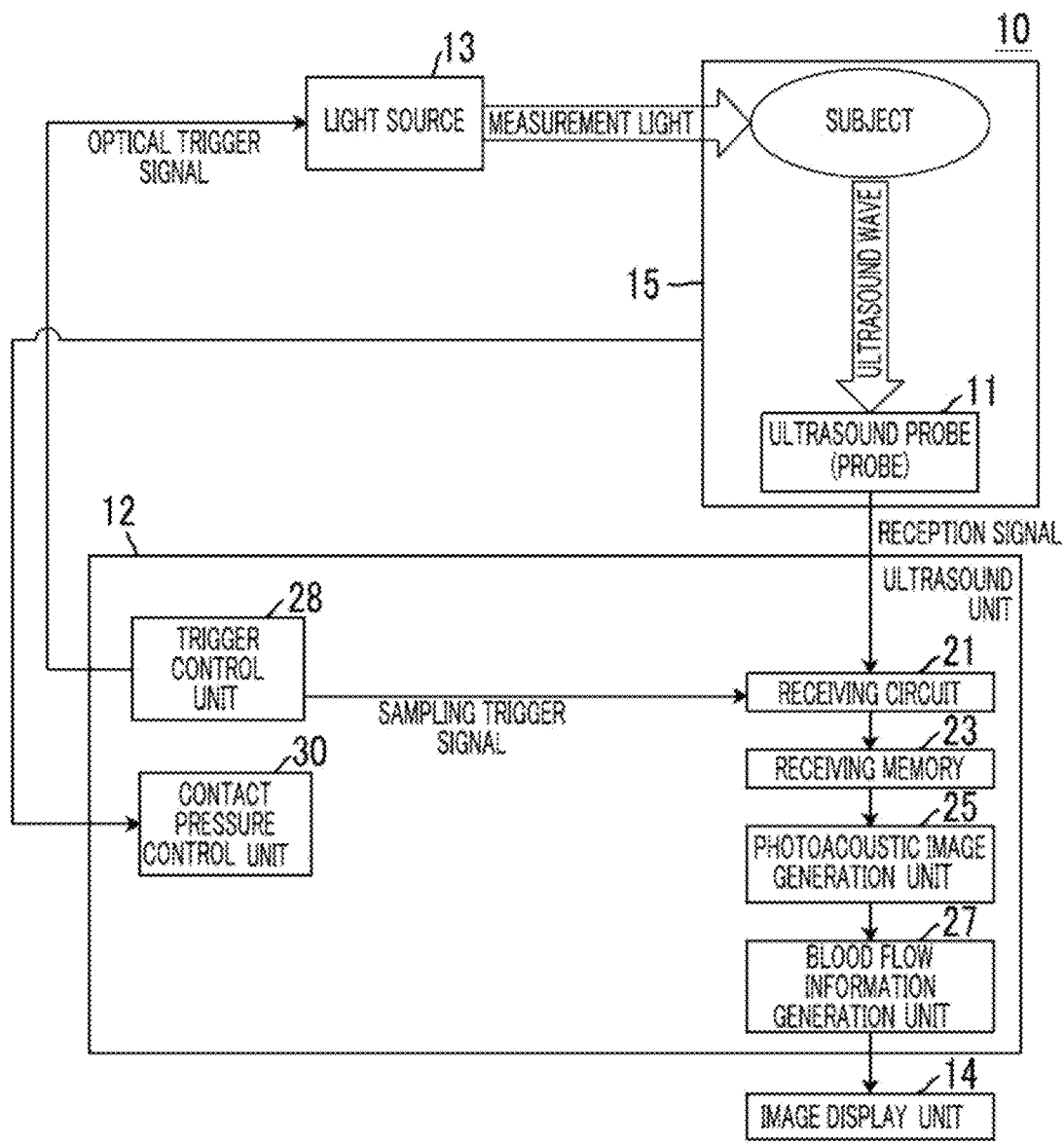
FIG. 2 is a block diagram showing the detailed configuration of the photoacoustic measurement system.

FIG. 2 shows the detailed configuration of a photoacoustic measurement system. In FIG. 2, the grip portion 51, the moving mechanism 52, and the pressure detection unit 53 of the stage 15 are not shown. The ultrasound unit 12 has a receiving circuit 21, a receiving memory 23, a photoacoustic image generation unit 25, a blood flow information generation unit 27, and a trigger control unit 28.

The receiving circuit 21 receives a detection signal output from the probe 11, and stores the received detection signal in the receiving memory 23. Typically, the receiving circuit 21 includes a low noise amplifier, a variable gain amplifier, a low pass filter, and an analog to digital converter (AD converter). The detection signal of the probe 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 23. The receiving circuit 21 is formed by one integral circuit (IC), for example. As the receiving memory 23, for example, a semiconductor memory is used.

The probe 11 outputs a detection signal of photoacoustic waves, and a detection signal (sampling data) of photoacoustic waves after AD conversion is stored in the receiving memory 23. The photoacoustic image generation unit 25 reads the detection signal of photoacoustic waves from the receiving memory 23, and generates a photoacoustic image based on the read detection signal of photoacoustic waves. The generation of a photoacoustic image includes, for example, image reconstruction such as phase matching addition, detection, and logarithmic conversion. For example, the photoacoustic image generation unit 25 is formed by large scale integration (LSI), such as a digital signal processor (DSP). The function of the photoacoustic image generation unit 25 may be realized by software processing using a processor included in the ultrasound unit 12.

The blood flow information generation unit 27 generates blood flow information based on the signal value of a photoacoustic image in a region of interest set in the photoacoustic image. The region of interest is set, for example, at a position away from the skin surface of the subject by a certain distance in the depth direction. The region of interest is preferably set to a region where capillaries are present. The blood flow information generation unit 27 generates blood flow information by scoring the signal value of the photoacoustic image in the region of interest. For example, a total value or an average value of the signal value of the photoacoustic image in the region of interest is calculated, and a score value based on the value is generated as blood flow information. Here, the signal value of the photoacoustic image is a value corresponding to the magnitude of the detection signal of the detected photoacoustic wave, and does not necessarily need to be the same as the pixel value of the photoacoustic image for display. Any signal in the photoacoustic image generation step can be used as the signal value of the photoacoustic image. Specifically, a detection signal of photoacoustic waves after reconstruction, a detection signal of photoacoustic waves after detection, and a detection signal of photoacoustic waves after logarithmic conversion may be used as the signal value of the photoacoustic image. The blood flow information generation unit 27 may further generate a graph showing the relationship between blood flow information and time. The blood flow information generation unit 27 may further generate a graph showing the relationship between blood flow information and the contact pressure of the probe 11. The blood flow information generation unit 27 is formed by a DSP, for example. The function of the blood flow information generation unit 27 may be realized by software processing using a processor included in the ultrasound unit 12.

The blood flow information generation unit 27 outputs the generated blood flow information to image display unit 14, such as a display device. The blood flow information generation unit 27 may output a graph showing the relationship between blood flow information and time to the image display unit 14. The blood flow information generation unit 27 may display a photoacoustic image and a region of interest on the image display unit 14.

The trigger control unit 28 controls each unit in the ultrasound unit 12. For example, in the case of acquiring a photoacoustic image, the trigger control unit 28 transmits an optical trigger signal to the light source 13 so that measurement light is emitted from the light source 13. In addition, the trigger control unit 28 controls the sampling start timing of photoacoustic waves or the like by transmitting a sampling trigger signal to the receiving circuit 21 in response to the emission of the measurement light. The area where photoacoustic waves are to be detected may be divided into a plurality of areas. In this case, emission of light to the subject and detection of photoacoustic waves are performed for each area. For example, the trigger control unit 28 is formed by a programmable logic device (PLD), such as a field-programmable gate array (FPGA).

A contact pressure control unit 30 drives the moving mechanism 52 based on the contact pressure detected by the pressure detection unit 53 (refer to FIG. 1). The contact pressure control unit 30 changes the contact pressure of the probe 11 by driving the moving mechanism 52. In addition, the contact pressure of the probe 11 is maintained at a certain pressure by driving the moving mechanism 52. For the contact pressure control unit 30, for example, an FPGA is used.

Measurement is performed in the following procedure. After the subject is placed on the stage 15, the contact pressure control unit 30 drives the moving mechanism 52 to press the probe 11 against the subject. The contact pressure control unit 30 moves the probe 11 in a direction in which the probe 11 is pressed against the subject, for example, until the contact pressure detected by the pressure detection unit 53 reaches a pressure equal to or greater than the systolic blood pressure, for example, 200 mmHg. After avascularization of a part to be examined, the trigger control unit 28 starts emission of measurement light and detection of photoacoustic waves. The emission of measurement light and the detection of photoacoustic waves are continued while maintaining the avascularized condition. After continuing the avascularized condition for a certain period of time, the contact pressure control unit 30 drives the moving mechanism 52 to move the probe 11 stepwise in a direction away from the subject. Through before and after the change in contact pressure, the emission of measurement light and the detection of photoacoustic waves are continued. A photoacoustic image is generated based on the detection signal of photoacoustic waves detected at each time, and blood flow information is generated. For example, an average value of the signal value of the photoacoustic image in the region of interest is generated as blood flow information. The number of regions of interest may be one or more. In a case where there are a plurality of regions of interest, blood flow information is generated for each region of interest.

FIG. 3 shows how a photoacoustic wave is detected. The grip portion 51 is, for example, an arm, and grips the probe 11. The moving mechanism 52 includes, for example, a ball screw and a motor for rotating the ball screw. The pressure detection unit 53 is, for example, a pressure sensor, and is provided between a moving portion moved by the ball screw and the grip portion 51. As the pressure sensor, for example, various known ones such as a strain gauge, a load cell, and a piezoelectric film can be used. The pressure detection unit 53 detects the contact pressure of the probe 11 with respect to a subject H at the grip portion 51. More specifically, in a connection portion between the grip portion 51 and the moving mechanism 52, the contact pressure of the probe 11 with respect to the subject H is detected. The detection signal of the pressure detection unit 53 is transmitted to the ultrasound unit 12.

FIG. 4 shows another example of the photoacoustic wave detection. In this example, the pressure detection unit 53 is provided between a rib R of the grip portion 51 and the arm. When the probe 11 is moved in a direction of the subject H by the moving mechanism 52, the rib R presses the arm to change the detection signal of the pressure detection unit 53. The position of the pressure detection unit 53 is not particularly limited, and any position is acceptable as long as the contact pressure of the probe 11 with respect to the subject H can be detected.

FIGS. 5A to 5C show a photoacoustic image and a region of interest. A region of interest ROI is set inside the subject in the depth direction. In particular, in a case where light having a wavelength of 755 nm is used as measurement light, photoacoustic waves emitted from the surface layer portion are strongly drawn in the photoacoustic image. Since a region of interest is set inside the subject in the depth direction, for example, a blood flow in a capillary or the like can be easily determined.

FIG. 5A shows a photoacoustic image at the time of avascularization. In the avascularized condition, a blood flow in the capillary is stopped. As a result, blood that is a light absorber is no longer present in the region of interest ROI. Since the number of light absorbers present in the region of interest ROI is small, the brightness of the region of interest ROI is low.

FIG. 5B shows a photoacoustic image when the contact pressure is reduced. When the contact pressure of the probe 11 is reduced stepwise to cause a stepwise change from the avascularized condition to the non-avascularized condition, perfusion of blood to the capillary gradually occurs. As a result, the amount of blood present in the region of interest is gradually increased. The signal value (brightness) in the region of interest ROI increases compared with that at the time of avascularization.

FIG. 5C shows a photoacoustic image at the time of non-avascularization. In the non-avascularized condition, perfusion of blood to the capillary occurs, and the amount of blood present in the region of interest is at the same level as before the avascularization. The signal value (brightness) in the region of interest ROI further increases to reach a certain level.

Figure 6:
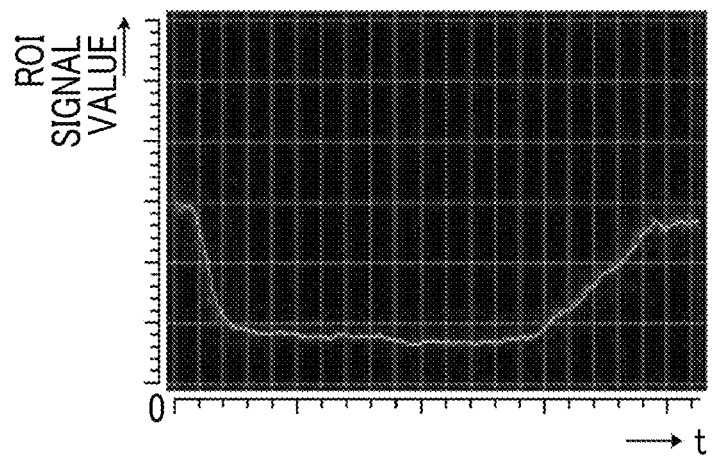
FIG. 6 is a graph showing a temporal change in the average signal value in a region of interest.

FIG. 6 is a graph showing a temporal change in the average signal value in the region of interest ROI. A condition at time t=0 is a non-avascularized condition, and is then changed to an avascularized condition. When the non-avascularized condition is changed to the avascularized condition, a blood flow in the capillary is stopped. As a result, blood that is a light absorber is no longer present in the region of interest. Therefore, as shown in the graph of FIG. 6, the average signal value in the region of interest (ROI signal value) decreases with time and reaches a value of a certain level. Thereafter, as the contact pressure is decreased stepwise, the ROI signal value increases with the decrease in contact pressure, and recovers to the level before the avascularization after becoming a non-avascularization condition.

Here, the intensity of a photoacoustic wave generated in the subject changes depending on the hemoglobin concentration and the oxygen saturation. In a case where light having a wavelength of 755 nm is used as the measurement light, the photoacoustic wave becomes weak as the blood volume decreases, and the photoacoustic wave becomes strong as the blood volume increases. In addition, the photoacoustic wave becomes strong as the oxygen saturation decreases, and the photoacoustic wave becomes weak as the oxygen saturation increases. When the non-avascularized condition is changed to the avascularized condition, the blood volume and the oxygen saturation are reduced. On the other hand, when the avascularized condition is changed to the non-avascularized condition, the blood volume and the oxygen saturation are increased. It is thought that the reason why the ROI signal value is reduced in the avascularized condition is that a reduction in the detection signal of the photoacoustic wave due to a reduction in blood volume is larger than an increase in the detection signal of the photoacoustic wave due to a reduction in oxygen saturation. In addition, it is thought that the reason why the ROI signal value increases in the non-avascularized condition is that an increase in the detection signal of the photoacoustic wave due to an increase in blood volume is larger than a reduction in the detection signal of the photoacoustic wave due to an increase in oxygen saturation.

Figure 7:
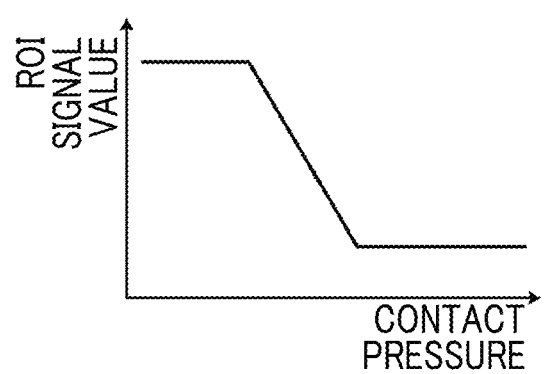
FIG. 7 is a graph showing the relationship between the ROI signal value and the contact pressure of a probe.

FIG. 7 is a graph showing the relationship between the ROI signal value and the contact pressure of the probe 11. When the ROI signal value is plotted with respect to the contact pressure of the probe 11, the graph shown in FIG. 7 is obtained. By referring to this graph, it is possible to know the contact pressure at which perfusion of blood starts, the inclination of the ROI signal value with respect to the contact pressure, the contact pressure at which the blood flow reaches a level before the avascularized condition, and the like. Therefore, it is possible to evaluate the perfusion of the subject.

Although an example in which the average value or the total value (ROI signal value) of the signal value of the photoacoustic image in the region of interest is used as blood flow information has been described above, the blood flow information is not limited thereto. Instead of using the ROI signal value itself as the blood flow information, a score value obtained by converting the ROI signal value using a look-up table, a function, or the like may be used as the blood flow information.

The blood flow information generation unit 27 may generate, as the blood flow information, a score value based on the difference between the maximum value and the minimum value of the ROI signal value within a certain period. Alternatively, the blood flow information generation unit 27 may generate, as the blood flow information, a score value based on the difference between the ROI signal value in the avascularized condition and the ROI signal value in the non-avascularized condition. Alternatively, the blood flow information generation unit 27 may generate, as the blood flow information, a score value based on a time change rate of the ROI signal value when the avascularized condition is changed to the non-avascularized condition. The time change rate can be calculated, for example, by differentiating the ROI signal value with time.

In addition, the blood flow information generation unit 27 may generate, as the blood flow information, a score value based on the time from the reference time to the time, at which the ROI signal value reaches a certain level, when the avascularized condition is changed to the non-avascularized condition. Alternatively, the blood flow information generation unit 27 may generate, as the blood flow information, a score value based on the ROI signal value at a time when a certain time has passed from the reference time when the avascularized condition is changed to the non-avascularized condition. The reference time may be, for example, a time at which the avascularized condition is changed to the non-avascularized condition. Alternatively, a time at which the contact pressure of the probe 11 starts to change stepwise may be set as the reference time. By using the blood flow information, it is possible to evaluate the extent or the speed of blood increase due to perfusion.

Here, since the ROI signal value depends on the intensity of the detection signal of the photoacoustic wave, the ROI signal value is strongly influenced by a relatively thick blood vessel having a large blood flow (having a large signal intensity) or the like. In order to evaluate the blood perfusion state of a fine blood vessel for nourishing the tissue, it is preferable to perform evaluation using an amount that does not depend on the signal intensity, for example, a binary amount. It is preferable that binarization is performed so as to distinguish between a range from a lower threshold value to an upper threshold value and the outside of the range. For example, the blood flow information generation unit 27 may binarize the signal value of the photoacoustic image by setting the signal value of the photoacoustic image to a first value (for example, a signal value 1) when the signal value of the photoacoustic image is equal to or greater than a first threshold value (corresponding to a lower threshold value) and equal to or less than a second threshold value (corresponding to an upper threshold value) larger than the first threshold value and setting the signal value of the photoacoustic image to a second value (for example, a signal value 0) when the signal value of the photoacoustic image is less than the first threshold value or greater than the second threshold value, and generate the blood flow information based on the binarized signal value of the photoacoustic image. More specifically, the blood flow information generation unit 27 may add binarized values in a region of interest and generate a value standardized by the area of the region of interest as the blood flow information.

In the present embodiment, a photoacoustic image is generated by performing light emission and photoacoustic wave detection in each of the avascularized condition and the non-avascularized condition, and blood flow information is generated based on the signal value of the photoacoustic image in the region of interest. In this manner, it is possible to generate blood flow information in a desired region using a photoacoustic image. In particular, by setting a region of interest inside the subject in the depth direction, it is possible to generate blood flow information for evaluating the perfusion in a deep part or a fine blood vessel without being influenced by artifacts on the subject surface or the like. In the present embodiment, avascularization of the subject is performed by the probe 11. Therefore, it is possible to evaluate the perfusion state without using a tourniquet separately. In addition, by plotting the blood flow information for the contact pressure, it is possible to evaluate a change in the blood flow information according to a change in the contact pressure.

Although an example in which light having a wavelength of 755 nm is mainly used as the measurement light has been described above, the wavelength of the measurement light is not limited thereto. For example, light having a wavelength of 1064 nm or 800 nm may be used as the measurement light.

The number of wavelengths of the measurement light is not limited to one, and measurement light having a plurality of wavelengths may be used. As described above, the intensity of the photoacoustic wave generated in the subject changes depending on the hemoglobin concentration and the oxygen saturation, and the manner of the change varies depending on the wavelength of the measurement light. For example, in a case where the wavelength of the measurement light is 755 nm, a stronger photoacoustic wave is generated from a vein having lower oxygen saturation between the artery and the vein. In a case where the wavelength of the measurement light is 1064 nm, a stronger photoacoustic wave is generated from the artery having higher oxygen saturation. In other words, in a case where the wavelength of the measurement light is 755 nm, the detection signal of the photoacoustic wave increases when the oxygen saturation is low. In a case where the wavelength of the measurement light is 1064 nm, the detection signal of the photoacoustic wave increases when the oxygen saturation is high. In a case where the wavelength of the measurement light is 800 nm, the generated photoacoustic wave hardly changes with the oxygen saturation. By detecting a photoacoustic wave using light having a wavelength of 755 nm and light having a wavelength of 1064 nm as the measurement light and examining the wavelength dependence of the detection signal of the photoacoustic wave, the blood flow and the oxygen saturation can be separated. The combination of wavelengths is not limited to those described above. For example, light having a wavelength of 755 nm and light having a wavelength of 800 nm may be used as the measurement light. Thus, since the blood flow and the oxygen saturation can be separated by using the measurement light having a plurality of wavelengths, the blood flow information generation unit 27 can generate blood flow information relevant to the oxygen saturation instead of or in addition to the blood flow information relevant to the blood flow.

Subsequently, a second embodiment of the present invention will be described. The configuration of a photoacoustic measurement system according to the third embodiment of the present invention is the same as the configuration of the photoacoustic measurement system 10 according to the first embodiment shown in FIGS. 1 and 2. In the present embodiment, the blood flow information generation unit 27 further generates a blood flow information image based on the blood flow information. Others may be the same as in the first embodiment.

In the present embodiment, a plurality of regions of interest are set in a photoacoustic image. For example, in a photoacoustic image, a plurality of regions of interest are set in a grid form in a region indicating an outer frame. The blood flow information generation unit 27 generates blood flow information for each of the plurality of regions of interest. The blood flow information image generated by the blood flow information generation unit 27 is a space map image for displaying the blood flow information of each region of interest in the region of interest. In the blood flow information image, each region of interest is displayed with a brightness corresponding to the blood flow information.

Figure 8:
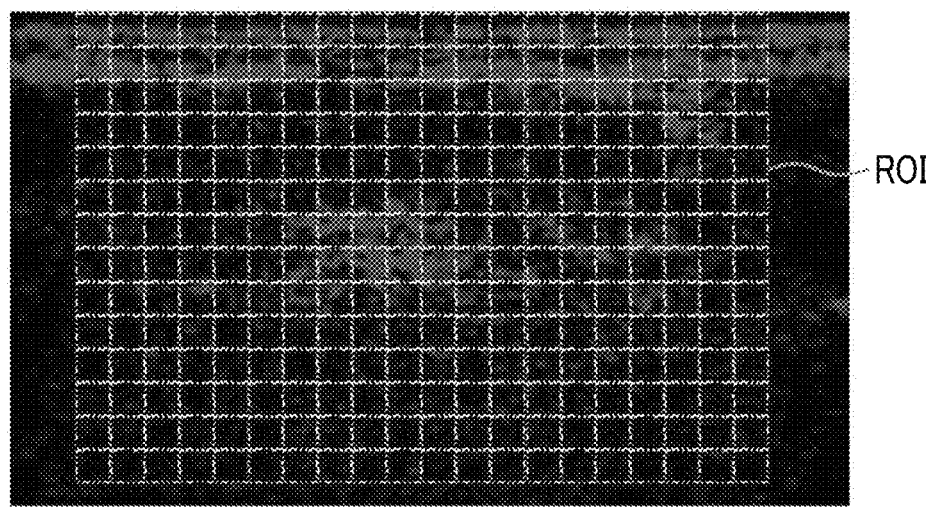
FIG. 8 is a diagram showing a plurality of regions of interest set in a grid form in a photoacoustic image.

FIG. 8 shows a plurality of regions of interest set in a grid form in a photoacoustic image. In the photoacoustic image, the regions of interest ROI are set in a grid form in a region indicating an outer frame. Since the regions of interest ROI are set in a grid form as described above, it is possible to evaluate the perfusion state of blood in the width direction and the depth direction of the image.

The blood flow information generation unit 27 generates, for example, a difference between the maximum value and the minimum value of the ROI signal value within a certain period, as blood flow information, for each of the regions of interest ROI in a grid form. For example, the ROI signal value is calculated by calculating the total value of the signal value of the photoacoustic image in the region of interest ROI and standardizing the total value with the area of the region of interest ROI. When calculating the total value of the signal value of the photoacoustic image in the region of interest ROI, the signal value of the photoacoustic image may be binarized. By referring to the blood flow image, it is possible to evaluate the amount of perfusion of blood in each part in the subject.

The blood flow information generation unit 27 generates a blood flow information image in time series, for example. In this case, the blood flow information generation unit 27 may set the display color of each region of interest in the blood flow information image to a different display color in a case where blood flow information at the first time is larger than blood flow information at the second time earlier than the first time and a case where the blood flow information at the first time is smaller than the blood flow information at the second time. One example of the first time is, for example, a current time. As a more specific example, the first time is a (current) time at which the blood flow information image is displayed on the screen. However, the first time is not limited thereto. For example, red may be set as a display color for a part where the blood flow is increasing and the blood flow information at the first time is larger than the blood flow information at the second time, and blue may be set as a display color for a part where the blood flow is decreasing and the blood flow information at the first time is smaller than the blood flow information at the second time. In this case, by referring to the blood flow image, it becomes easy to understand in which part the blood has increased and in which part the blood has decreased.

In the present embodiment, a blood flow information image is generated based on blood flow information. By imaging the blood flow information, it becomes easy to grasp the spatial distribution of blood flow information. In particular, in the case of comparing a plurality of regions of interest ROI, it becomes easy to compare the local behaviors of the overall behavior by map-displaying the blood flow information of the region of interest ROI corresponding to the position of the region of interest ROI of the photoacoustic image. Other effects are the same as in the first embodiment.

Figure 9:
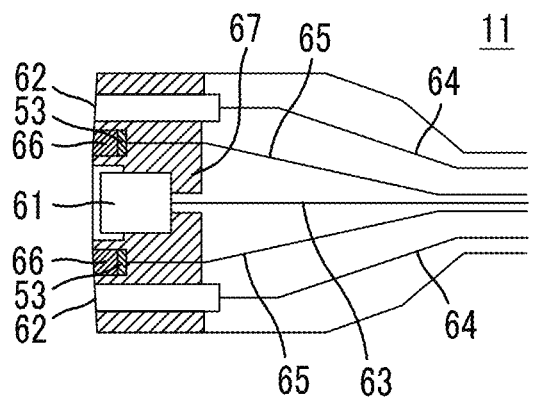
FIG. 9 is a cross-sectional view showing a probe used in a photoacoustic measurement system according to a third embodiment of the present invention.

Subsequently, a third embodiment of the present invention will be described. FIG. 9 shows a probe 11 used in a photoacoustic measurement system according to the third embodiment of the present invention. In the present embodiment, the probe 11 has the pressure detection unit 53. Others may be the same as those in the first embodiment or the second embodiment.

The probe 11 includes a detector element 61, a light emitting portion 62, and the pressure detection unit 53. The detector element 61, the light emitting portion 62, and the pressure detection unit 53 are fixed by a support member 67. The detector element 61 is, for example, a piezoelectric element formed of a polymer film, such as piezoelectric ceramics or polyvinylidene fluoride (PVDF). The detection signal of the detector element 61 is transmitted to the ultrasound unit 12 (refer to FIGS. 1 and 2) through a signal wiring 63. The light emitting portion 62 is formed by the end surface of a light guide plate on the light emitting side. The measurement light emitted from the light source 13 (refer to FIGS. 1 and 2) is guided to the probe 11 by the optical wiring, such as an optical fiber 64, and is emitted toward the subject from the end surface (light emitting portion) of the light guide plate on the light emitting side.

The pressure detection unit 53 is disposed between the detector element 61 and the light emitting portion 62. For example, as shown in FIG. 9, the pressure detection unit 53 is disposed at a position on a back side from the surface of the probe 11 in contact with the subject. It is preferable that the pressure detection unit 53 is covered with a cover 66 that is in contact with the subject with ultrasound jelly or water interposed therebetween. The detection signal of the pressure detection unit 53 is transmitted to the ultrasound unit 12 through a sensor signal line 65.

Figure 10:
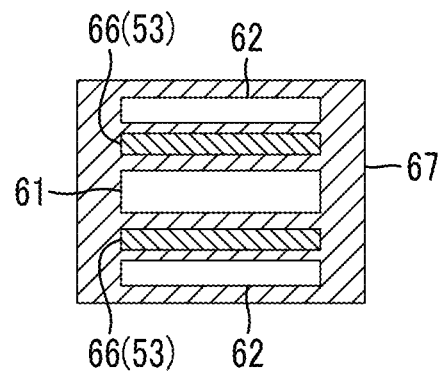
FIG. 10 is an external view showing a surface of the probe in contact with a subject.

FIG. 10 is an external view showing the surface of the probe 11 in contact with the subject. The cover 66 is provided on the surface of the support member 67, and the pressure detection unit 53 is provided at the back of the cover 66. The length of the pressure detection unit 53 in the longitudinal direction is almost equal to the lengths of the detector element 61 and the light emitting portion 62 in the longitudinal direction. When the probe 11 is pressed against the subject, the pressure detection unit 53 detects the contact through the cover 66.

Figure 11:
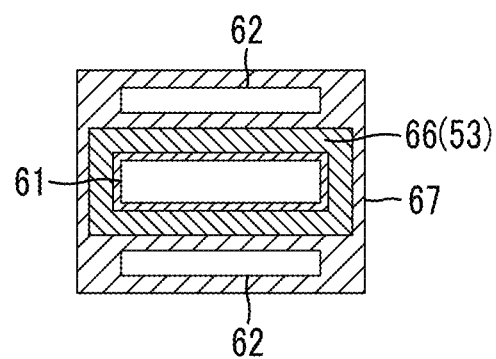
FIG. 11 is an external view showing another example of the surface of the probe in contact with a subject.

FIG. 11 is an external view showing another example of the surface of the probe 11 in contact with the subject. In this example, the pressure detection unit 53 is provided at the probe so as to surround the detector element 61. As shown in this example, the entire pressure detection unit 53 does not need to be disposed between the detector element 61 and the light emitting portion 62, and at least a part of the pressure detection unit 53 may be disposed between the detector element 61 and the light emitting portion 62.

In the present embodiment, the probe 11 has the pressure detection unit 53. In this case, it is not necessary to provide the pressure detection unit 53 in the stage 15 (refer to FIG. 1). Since the pressure detection unit 53 is built into the probe 11, it is also possible to perform measurement by pressing the probe 11 against the subject manually, for example.

Figure 12:
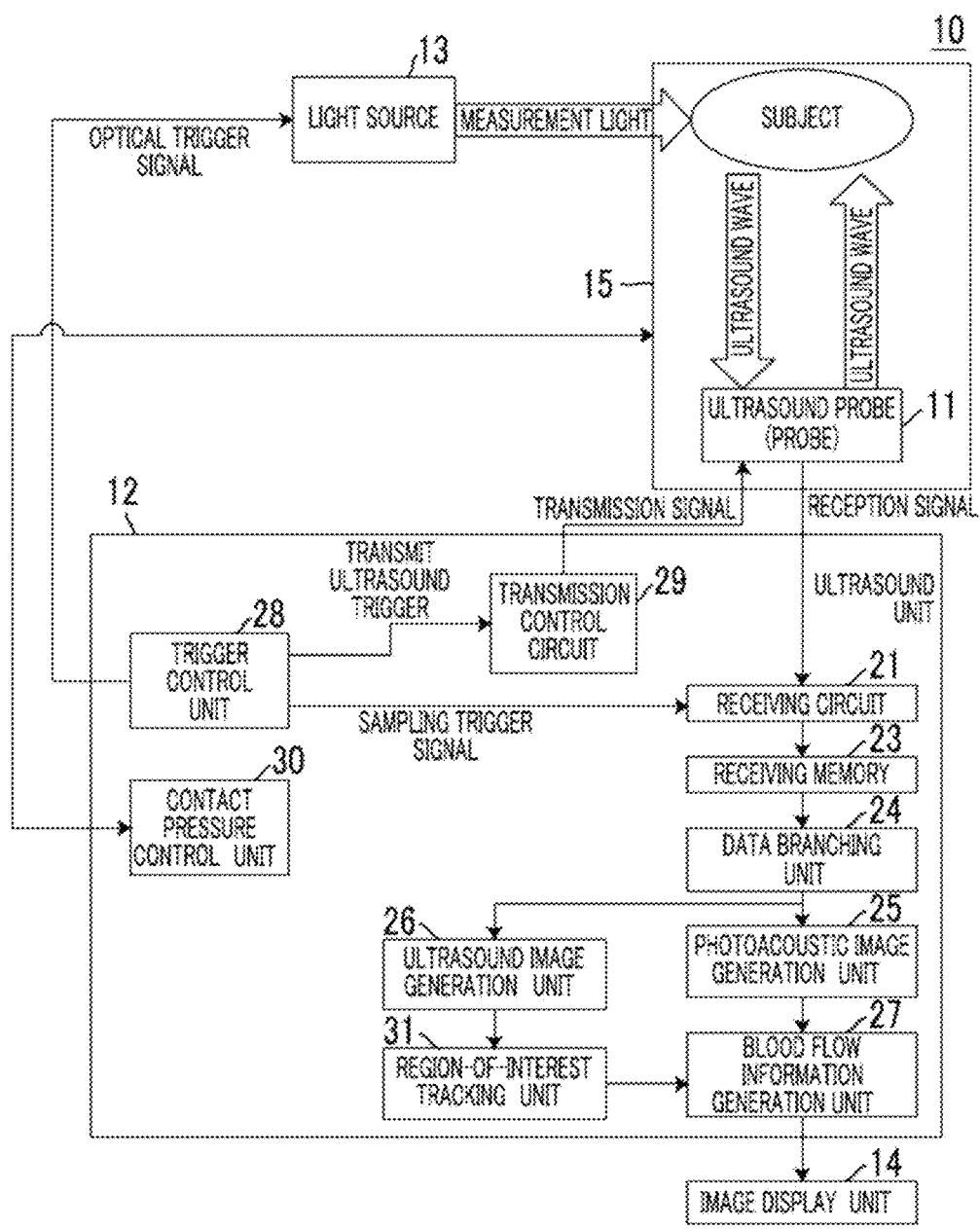
FIG. 12 is a block diagram showing a photoacoustic measurement system according to a fourth embodiment of the present invention.

Subsequently, a fourth embodiment of the present invention will be described. FIG. 12 shows a photoacoustic measurement system according to the fourth embodiment of the present invention. A photoacoustic measurement system 10 of the present embodiment is different from the photoacoustic measurement system 10 of the first embodiment shown in FIG. 2 in that the ultrasound unit 12 further has a data branching unit 24, an ultrasound image generation unit 26, a transmission control circuit 29, and a region-of-interest tracking unit 31. Others may be the same as those in the first to third embodiments. In the embodiment of the present invention, an ultrasound wave is used as an acoustic wave. However, the acoustic wave is not limited to the ultrasound wave, and an acoustic wave having an audible frequency may be used as long as an appropriate frequency can be selected according to an examination target, measurement conditions, or the like.

In the present embodiment, in addition to the detection of photoacoustic waves, the probe 11 performs transmission of acoustic waves (ultrasound waves) to the subject and reception of reflected acoustic waves (reflected ultrasound waves) of the transmitted ultrasound waves. Transmission and reception of ultrasound waves may be performed at separate positions. For example, ultrasound waves may be transmitted from a position different from the probe 11, and reflected ultrasound waves of the transmitted ultrasound waves may be received by the probe 11.

The probe 11 outputs a detection signal of photoacoustic waves and a detection signal of reflected ultrasound waves, and detection signals (sampling data) of photoacoustic waves and reflected ultrasound waves after AD conversion are stored in the receiving memory 23. The data branching unit 24 is, for example, a changeover switch, and transmits the sampling data of the detection signal of photoacoustic waves read from the receiving memory 23 to the photoacoustic image generation unit 25. In addition, the sampling data of the reflected ultrasound waves read from the receiving memory 23 is transmitted to the ultrasound image generation unit 26. The ultrasound image generation unit (reflected acoustic wave image generation unit) 26 generates an ultrasound image (reflected acoustic wave image) based on the detection signal of reflected ultrasound waves detected by the probe 11. The generation of an ultrasound image also includes image reconstruction such as phase matching addition, detection, and logarithmic conversion. The generated ultrasound image may be displayed on the image display unit 14.

In the case of acquiring an ultrasound image, the trigger control unit 28 transmits an ultrasound wave transmission trigger signal for giving an instruction to transmit ultrasound waves to the transmission control circuit 29. When the ultrasound wave transmission trigger signal is received, the transmission control circuit 29 makes the probe 11 transmit ultrasound waves. The probe 11 detects reflected ultrasound waves by performing a scan while shifting the acoustic line by one line at a time, for example. The trigger control unit 28 transmits a sampling trigger signal to the receiving circuit 21 according to the timing of ultrasound wave transmission, thereby starting the sampling of reflected ultrasound waves. Acquisition of a photoacoustic image and acquisition of an ultrasound image may be performed in synchronization with each other.

Here, since the position of the subject changes due to body motion or the like, the position of the region of interest of the photoacoustic image may change between frames. An ultrasound image is used for correction of positional deviation between frames. The region-of-interest tracking unit 31 tracks the position of the region of interest using the ultrasound image. In particular, the region-of-interest tracking unit 31 tracks the position of the region of interest using a plurality of consecutive ultrasound images (a plurality of consecutive frames). The region-of-interest tracking unit 31 detects motion of an image between frames using a method, such as template matching between frames, for example. The region-of-interest tracking unit 31 moves the position of the region of interest by the amount of detected motion of the image between the frames, and notifies the blood flow information generation unit 27 of the moved position of the region of interest. The blood flow information generation unit 27 generates blood flow information using the notified position of the region of interest. In generating blood flow information, it is preferable that the region of interest does not include a region outside the body. It is preferable to detect a skin boundary in a region of interest in the ultrasound image generated in synchronization with the photoacoustic image and set a part in a direction of the inside of the subject rather than the skin boundary as the area of the region of interest.

In the present embodiment, the ultrasound image generation unit 26 generates an ultrasound image. By using the ultrasound image, it is possible to detect the motion of the image between the frames and track the region of interest between the frames. In this case, even when a positional deviation occurs due to body motion or the like, it is possible to generate the blood flow information of the same part in the subject. Therefore, it is possible to improve the accuracy of the generated blood flow information. Other effects are the same as those of the first to third embodiments.

While the present invention has been described based on the preferred embodiments, the photoacoustic measurement apparatus and the photoacoustic measurement system of the present invention are not limited to the above embodiments, and various modifications and changes in the configurations of the above embodiments are also included in the range of the present invention.

EXPLANATION OF REFERENCES

10: photoacoustic measurement system
11: probe
12: ultrasound unit
13: light source
14: image display unit
15: stage
21: receiving circuit
23: receiving memory
24: data branching unit
25: photoacoustic image generation unit
26: ultrasound image generation unit
27: blood flow information generation unit
28: trigger control unit
29: transmission control circuit
30: contact pressure control unit
31: region-of-interest tracking unit
51: grip portion
52: moving mechanism
53: pressure detection unit
61: detector element
62: light emitting portion
63: signal wiring
64: optical fiber
65: sensor signal line
66: cover
67: support member

What is claimed is:

1. A photoacoustic measurement apparatus, comprising:
a probe that detects a photoacoustic wave generated in a subject by measurement light emitted to the subject;
a grip portion that grips the probe;
a pressure sensor for detecting a contact pressure of the probe with respect to the subject;
a moving mechanism comprising a motor and is driven by the motor that is configured to move the probe in a direction in which the probe is pressed against the subject until the contact pressure representing the subject is avascularized condition based on the contact pressure, and a direction in which the probe is away from the subject until the contact pressure representing the subject is non-avascularized condition through the grip portion; and
a processor configured to:
generate a photoacoustic image based on a detection signal of the photoacoustic wave detected by the probe; and
generate blood flow information based on a signal value of the photoacoustic image in a region of interest set in the photoacoustic image,
wherein the probe detects the photoacoustic wave in each of at least an avascularized condition in which the subject is avascularized by the probe and a non-avascularized condition in which the subject is not avascularized.

2. The photoacoustic measurement apparatus according to claim 1, further comprising:
a contact pressure control circuit for driving the moving mechanism based on the contact pressure detected by the pressure sensor.

3. The photoacoustic measurement apparatus according to claim 1,
wherein the pressure sensor detects the contact pressure at the grip portion.

4. The photoacoustic measurement apparatus according to claim 1,
wherein the pressure sensor is provided at the probe.

5. The photoacoustic measurement apparatus according to claim 4,
wherein the probe includes a detector element that detects the photoacoustic wave and a light emitting portion that emits the measurement light, and
at least a part of the pressure sensor is provided between the detector element and the light emitting portion.

6. The photoacoustic measurement apparatus according to claim 5,
wherein the pressure sensor surrounds the detector element.

7. The photoacoustic measurement apparatus according to claim 4,
wherein the pressure sensor is covered with a cover in contact with the subject.

8. The photoacoustic measurement apparatus according to claim 1,
wherein the processor is further configured to binarize the signal value by setting the signal value to a first value when the signal value is equal to or greater than a first threshold value and equal to or less than a second threshold value larger than the first threshold value and setting the signal value to a second value different from the first value when the signal value is less than the first threshold value or greater than the second threshold value, and generates the blood flow information based on the binarized signal value.

9. The photoacoustic measurement apparatus according to claim 1,
wherein the probe further detects a reflected acoustic wave with respect to an acoustic wave transmitted to the subject,
wherein the processor is further configured to generate a reflected acoustic wave image based on a detection signal of the reflected acoustic wave detected by the probe; and
wherein processor is further configured to track a position of the region of interest using the reflected acoustic wave image.

10. The photoacoustic measurement apparatus according to claim 1,
wherein the processor is further configured to generate, as blood flow information, a total value or an average value of the signal value in the region of interest.

11. The photoacoustic measurement apparatus according to claim 10,
wherein the processor is further configured to generate a graph showing a relationship between the blood flow information and the contact pressure.

12. The photoacoustic measurement apparatus according to claim 1,
wherein the processor is further configured to calculate a total value or an average value of the signal value in the region of interest, and generates, as the blood flow information, a score value based on a difference between a minimum value and a maximum value of the total value or the average value in a certain period.

13. The photoacoustic measurement apparatus according to claim 1,
wherein the processor is further configured to generate, as the blood flow information, a score value based on a difference between a total value or an average value of the signal value in the region of interest in the avascularized condition and a total value or an average value of the signal value in the region of interest in the non-avascularized condition.

14. The photoacoustic measurement apparatus according to claim 1,
wherein, in a case where the subject is changed from the avascularized condition to the non-avascularized condition by the probe, the processor is further configured to generate, as the blood flow information, a score value based on a time change rate of a total value or an average value of the signal value in the region of interest.

15. The photoacoustic measurement apparatus according to claim 1,
wherein, in a case where the subject is changed from the avascularized condition to the non-avascularized condition by the probe, the processor is further configured to generate, as the blood flow information, a score value based on a total value or an average value of the signal value in the region of interest after a certain time has passed from a reference time.

16. The photoacoustic measurement apparatus according to claim 1,
wherein, in a case where the subject is changed from the avascularized condition to the non-avascularized condition by the probe, the processor is further configured to generate, as the blood flow information, a score value based on a time from a reference time to a time at which a total value or an average value of the signal value in the region of interest reaches a certain level.

17. The photoacoustic measurement apparatus according to claim 1,
wherein the processor is further configured to generate a blood flow information image based on the blood flow information.

18. The photoacoustic measurement apparatus according to claim 17,
wherein, in a case where a plurality of the region of interest are set, the blood flow information is generated for each of the plurality of region of interest, and the blood flow information image is a space map image for displaying blood flow information of each region of interest in the region of interest.

19. The photoacoustic measurement apparatus according to claim 18,
wherein, in the blood flow information image, each region of interest is displayed with a brightness corresponding to the blood flow information.

20. The photoacoustic measurement apparatus according to claim 18,
wherein the processor is further configured to set a display color of each region of interest in the blood flow information image to a different display color in a case where blood flow information at a first time is larger than blood flow information at a second time earlier than the first time and a case where the blood flow information at the first time is smaller than the blood flow information at the second time.

21. The photoacoustic measurement apparatus according to claim 1,
wherein a plurality of the region of interest are set in a grid form.

22. A photoacoustic measurement system, comprising:
a light source that emits measurement light; and
the photoacoustic measurement apparatus according to claim 1.

23. The photoacoustic measurement apparatus according to claim 1, wherein the moving mechanism includes a screw.

* * * * *